United States Patent

Kimura et al.

Patent Number: 5,837,884
Date of Patent: Nov. 17, 1998

[54] HUMIDITY SENSOR USING TEMPERATURE SENSING RESISTOR CONTROLLED TO BE AT CONSTANT TEMPERATURE OF MORE THAN 150° C.

[75] Inventors: Mitsuteru Kimura, 2-56 Shiomidai 3-chome, Shichigahama-machi, Miyagi-gun Miyagi 985; Mituyuki Takeda; Hiroyuki Sato, both of Sendai, all of Japan

[73] Assignees: Tokin Corporation; Mitsuteru Kimura, both of Miyagi, Japan

[21] Appl. No.: 702,602

[22] PCT Filed: Dec. 27, 1995

[86] PCT No.: PCT/JP95/02727

§ 371 Date: Aug. 23, 1996

§ 102(e) Date: Aug. 23, 1996

[87] PCT Pub. No.: WO96/21146

PCT Pub. Date: Jul. 11, 1996

[30] Foreign Application Priority Data

Dec. 29, 1994 [JP] Japan ................... 6-338974
Dec. 29, 1994 [JP] Japan ................... 6-338975

[51] Int. Cl.⁶ .................................................. G01N 25/56
[52] U.S. Cl. ............................................. 73/25.4; 73/335.2
[58] Field of Search ..................... 73/25.04, 24.04, 73/29.01, 29.02, 335.02, 335.05; 338/35

[56] References Cited

U.S. PATENT DOCUMENTS

| | | | |
|---|---|---|---|
| 4,419,021 | 12/1983 | Terada et al. | 374/101 |
| 4,532,797 | 8/1985 | Yang . | |
| 4,734,554 | 3/1988 | Tateda et al. | 219/10.55 |
| 4,768,378 | 9/1988 | Ando et al. | 73/336.5 |
| 4,817,414 | 4/1989 | Hagen et al. . | |
| 4,911,357 | 3/1990 | Kitamura | 236/44 |
| 4,918,974 | 4/1990 | Hachey et al. . | |
| 5,048,336 | 9/1991 | Sugihara et al. | 73/29.01 |
| 5,345,184 | 9/1994 | Andoh | 324/720 |
| 5,551,283 | 9/1996 | Manaka et al. | 73/31.01 |

FOREIGN PATENT DOCUMENTS

| | | |
|---|---|---|
| 0 382 414 | 8/1990 | European Pat. Off. . |
| 3-61843 | 3/1991 | Japan . |
| 5-223770 | 8/1993 | Japan . |
| 5-288705 | 11/1993 | Japan . |
| 7-55748 | 3/1995 | Japan . |

Primary Examiner—Hezron E. Williams
Assistant Examiner—Jay L. Politzer
Attorney, Agent, or Firm—Frishauf, Holtz, Goodman, Langer & Chick

[57] ABSTRACT

A humidity sensor of a heat conduction type which enables a humidity measurement to be produced by a single temperature sensing resistor so as to reduce a change in characteristic depending on a temperature change of the measurement atmosphere and to reduce the cost, comprises a temperature sensing resistor 1 and three fixed resistors $R_1$, $R_2$ and $R_3$ which form a Wheatstone bridge circuit. The humidity is measured by utilizing the fact that the heat dissipation of the temperature sensing resistor 1 changes depending on the humidity. The temperature sensing resistor 1 is heated by a heat generator 2 for self-radiation of Joule heat so that the temperature of the temperature sensing resistor 1 is controlled to be at a constant temperature of 150° C. or more. The output voltage value of the Wheatstone bridge circuit is corrected with reference to the variation of the output voltage value depending on the ambient temperature of the temperature sensing resistor 1.

12 Claims, 12 Drawing Sheets

HUMIDITY SENSOR USING TEMPERATURE SENSING RESISTOR CONTROLLED TO BE AT CONSTANT TEMPERATURE OF MORE THAN 150° C.

FIELD OF THE INVENTION

This invention relates to a humidity sensor for detecting the quantity of water vapor in an atmosphere for use in an air conditioner, a dehumidifier, a cooker, a cultivation house, and so on.

BACKGROUND ART

Recently, there has been an increasing demand for detecting and controlling the humidity such as the relative humidity and the absolute humidity in an air conditioner, a dehumidifier, a humidifier, a cooker, a cultivation house, and so on. To meet the demand, various types of humidity sensors have been proposed.

Conventional humidity sensors include an electrical resistance type or a capacitance type which utilizes the change in electric characteristic depending on moisture absorption of a humidity sensing material, a heat conduction type which detects the change in heat conductivity of the air depending on presence or absence of water vapor in the air, and the like. The heat conduction type is excellent in long-term stability because of no moisture absorption.

As shown in FIG. 1, a conventional humidity sensor comprises a Wheatstone bridge circuit formed by a temperature sensing resistor 31 having a resistance value $R_{4H}$, a temperature sensing resistor 32 having a resistance value $R_{4T}$, and fixed resistors $R_{41}$, $R_{42}$, $R_{43}$, and $R_{4S}$, and measures the humidity by utilizing the fact that the heat radiation of the temperature sensing resistors 31 and 32 varies depending upon the humidity. It is noted here that $R_{4S}$ is not necessary in case where a temperature sensing resistor, such as a platinum resistor, having a positive temperature characteristic is used as each fixed resistor. The temperature-resistance characteristics of $R_{4T}$ and $R_{4H}$ must be identical. The resistance values of $R_{41}$ and $R_{42}$ must be equal, too.

In the above-mentioned humidity sensor, the temperature sensing resistor 31 is exposed in the outside air while the temperature sensing resistor 32 is sealed in a dry atmosphere. In this state, a voltage $V_{4IN}$ applied to the temperature sensing resistors 31 and 32 makes a current flow through the temperature sensing resistors 31 and 32 which then generate the Joule heat to have temperatures higher than the ambient temperature. The temperatures of the temperature sensing resistors 31 and 32 are determined by electric power applied to the temperature sensing resistors 31 and 32 and heat radiation of the temperature sensing resistors 31 and 32, respectively.

When water vapor is contained in the outside air, the heat radiation becomes large under the influence of the heat conduction of the water vapor, as compared with the case where no water vapor is contained in the outside air. Therefore, the temperature of the temperature sensing resistor 31 becomes lower than that of the temperature sensing resistor 32. As a result, a potential difference $V_{4OUT}$ is produced across the fixed resistor $R_{43}$. By the use of this phenomenon, it is possible to detect the absolute humidity in the air.

The conventional humidity sensor of a heat conduction type has a structure illustrated in an exploded perspective view of FIG. 2 and a perspective view of FIG. 3. Referring to FIGS. 2 and 3, each of the temperature sensing resistors 31 and 32 comprises a platinum thin film formed on an alumina substrate. In place of the platinum thin film, the temperature sensing resistors 31 and 32 may be made of any other material having a resistance value which vary following the temperature change.

The conventional humidity sensor of a heat conduction type is manufactured as follows. As shown in FIG. 2 and FIG. 3, the temperature sensing resistors 31 and 32 are fixed on different stems 34 through supports 314 by means of bonding with an adhesive or welding. Thereafter, connection of terminals is carried out by wire bonding. The stem 34 with the temperature sensing resistor 31 fixed thereto is covered with a cap 33a having ventilation holes 35 by welding. As the adhesive, an inorganic or organic adhesive is selectively used depending on the temperature.

On the other hand, the temperature sensing resistor 32 is sealed in dry air by covering the stem 34 with a cap 33b at a low temperature of −40° C. and thereafter welding the stem 34 and the cap 33b to each other. Thereafter, the caps 33a and 33b are press-fitted in a cap fixing plate 36. Subsequently, an outer periphery of the cap fixing plate 36 is covered with a metal case 311 and a metal cover 310 is attached thereon. Thus, the humidity sensor is completed.

However, the conventional humidity sensor uses the two temperature sensing resistors and it is difficult to make the characteristics of the two temperature sensing resistors be equal to each other. It is therefore difficult to reduce the change in characteristic depending on the temperature change. It is also difficult to reduce the cost because the structure for maintaining the uniform temperature distribution in an atmosphere of each temperature sensing resistor is complicated.

It is therefore an object of this invention to provide a humidity sensor of a heat conduction type which enables humidity measurement by a single temperature sensing resistor so as to reduce the change in characteristic depending on the temperature change in a measurement atmosphere and to reduce the cost.

SUMMARY OF THE INVENTION

According to this invention, there is provided a humidity sensor for measuring humidity by utilizing the fact that the heat dissipation of a temperature sensing resistor changes depending on the humidity, the humidity sensor comprising a heating control unit which includes a heat generator for self-radiation of Joule heat and being arranged to heat the temperature sensing resistor, the heat generator heating the temperature sensing resistor to control the temperature of the temperature sensing resistor to be at a constant temperature as a first temperature, the first temperature being more than 150° C. An electrical circuit produces an output voltage relating to voltage drop across the temperature sensing resistor at the first temperature. A correcting means is provided for correcting the output voltage value of the electrical circuit with reference to the variation in output voltage value of the electrical circuit depending on the ambient temperature of the temperature sensing resistor.

In the humidity sensor according to this invention, it is preferred that the heating control unit comprises switching means for switching the temperature of the temperature sensing resistor between the first temperature and a second temperature lower than the first temperature by applying two kinds of pulse voltages to the heat generator within a predetermined period, that the electrical circuit produces the output voltage relating to the voltage drop across the temperature sensing resistor when the temperature of the temperature sensing resistor is selected at the second temperature, and that the correcting means corrects, with reference to the output characteristic of the electrical circuit, the output voltage value of the electrical circuit when the temperature of the temperature sensing resistor is selected at the first temperature, so as to remove the influence of the temperature of a measurement atmosphere.

BEST MODE FOR EMBODYING THE INVENTION

Figure 1:
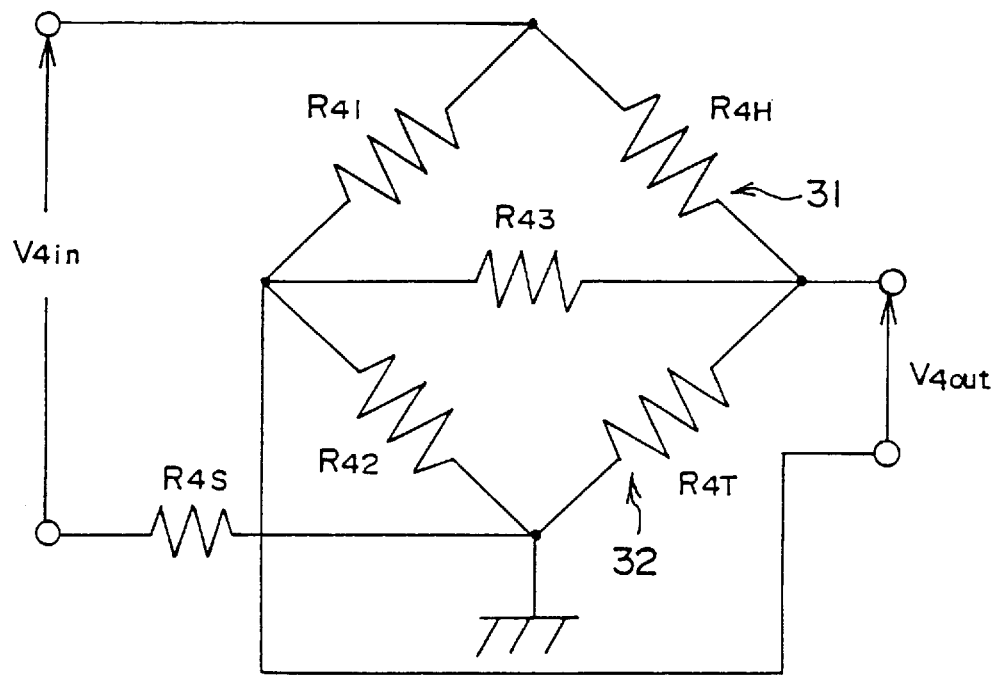
FIG. 1 is a circuit diagram showing an example of a conventional humidity sensor.

Next, description will be made in detail as regards this invention with reference to the drawing.

Figure 4:
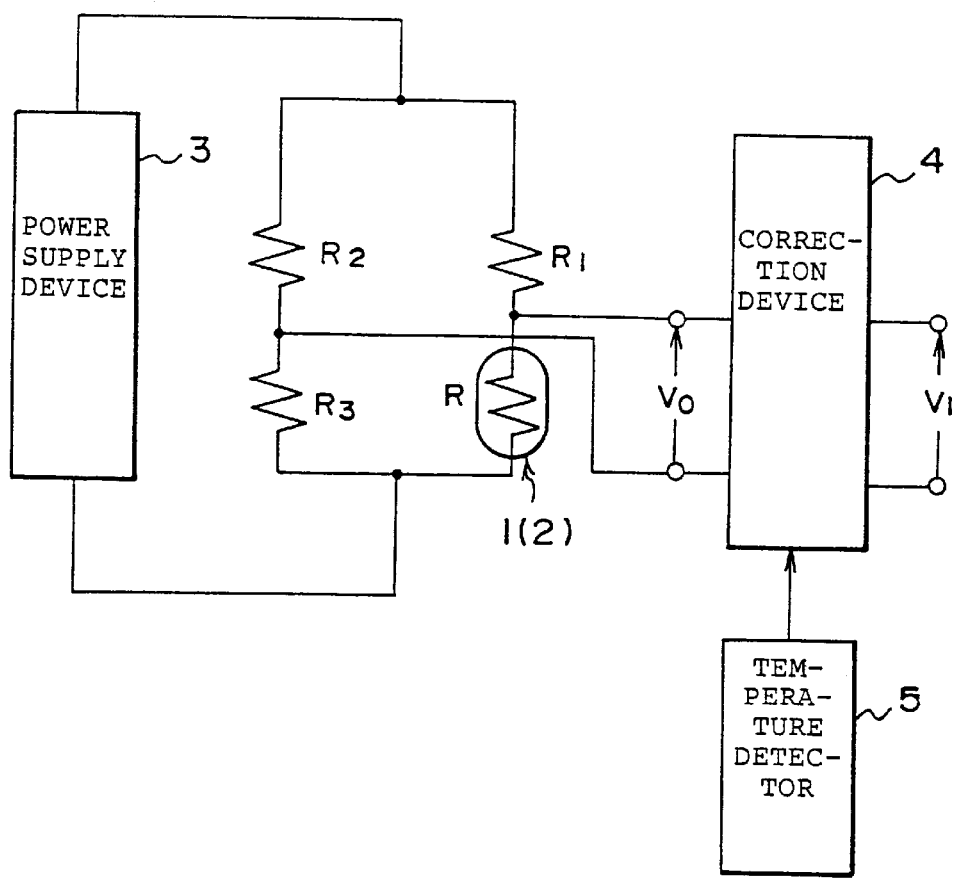
FIG. 4 is a circuit diagram showing a humidity sensor according to an embodiment of this invention.

Referring to FIG. 4, a humidity sensor according to an embodiment of this invention comprises a temperature sensing resistor 1 which also serves as a heat generator 2 and which has a resistance value R. The sensor also comprises the three fixed resistors $R_1$, $R_2$, and $R_3$. Among the fixed resistors, $R_2=R_3$ is satisfied. The temperature sensing resistor 1 and the three fixed resistors $R_1$, $R_2$, and $R_3$ form a Wheatstone bridge circuit which is an electronic circuit. This humidity sensor is for measuring the humidity by utilizing the fact that the heat radiation of the temperature sensing resistor 1 changes depending on the humidity. The Wheatstone bridge circuit has an input terminal connected to a power supply device 3. An output terminal of the Wheatstone bridge circuit is connected to a correction device 4. The correction device 4 is connected to a temperature detector 5 for detecting the temperature in a measurement atmosphere. The temperature detector 5 supplies the correction device 4 with information of the temperature in the measurement atmosphere. The power supply device 3 forms a heating control portion which applies a d.c. voltage to the temperature sensing resistor 1 also serving as the heat generator 2 for self-radiation of Joule heat to flow a current therethrough, thereby heating the temperature sensing resistor 1 so that the temperature of the temperature sensing resistor 1 is controlled at a constant temperature of 300° C. or more. The correction device 4 corrects an output voltage value $V_0$ of the Wheatstone bridge circuit with reference to the variation of the output voltage value $V_0$ depending on the ambient temperature of the temperature sensing resistor 1 to produce an output voltage value $V_1$.

Description will now be made in detail as regards a measurement principle of the humidity sensor according to the one embodiment of this invention.

Assuming that the temperatures of the temperature sensing resistor 1 and a humidity sensitive portion are approximately equal to each other, a temperature rise $\Delta T$ of the temperature sensing resistor element 1 in a stationary state is represented by the following formula 1:

$$\alpha \cdot S \cdot \Delta T = V_0^2 / R \quad (1)$$

Herein, $\alpha$ is a heat transmission coefficient, S, a constant determined depending on an area and a shape of the humidity sensitive portion, $V_0$, an output voltage, and R, a resistance value of the temperature sensing resistor.

Letting the temperature of the temperature sensing resistor 1 and the ambient temperature be represented by T and $T_0$, respectively, $\Delta T$ is represented by the following formula 2:

$$\Delta T = T - T_0 \quad (2)$$

From the above-mentioned formulas 1 and 2, the following formula 3 is obtained:

$$V_0 = [\alpha \cdot S \cdot (T - T_0) \cdot R]^{1/2} \quad (3)$$

Herein, $\alpha \cdot S$ is represented by the following formula 4:

$$\alpha \cdot S = \beta \cdot \lambda \quad (4)$$

Herein, $\beta$ is a constant and $\lambda$ is a heat conductivity of the ambient atmosphere of the temperature sensing resistor 1.

Between 100° C. and 150° C., the heat conductivity $\lambda$ hardly depends on the amount of water vapor within a humidity range between 0 and 300 g/m³. This is also proved from a theoretical formula representing the vapor concentration dependency of the heat conductivity $\lambda$ within the above-mentioned humidity range in a system containing water vapor mixed with pure air. Thus, the value of $V_0$ at a temperature ranging between 100° C. and 150° C. does not depend on the humidity. It is therefore required that the temperature T of the temperature sensing resistor 1 is held at 150° C. or more.

Next, description will be made as regards a first correction method of correcting $V_0$ into $V_1$.

Since the value of S fluctuates depending on each sample, consideration will be made about, for example, the sample having a constant S' depending on the area and the shape of the humidity sensitive portion. Letting the output voltage value of the Wheatstone bridge circuit be represented by $V_0'$, the value of $\alpha$ in the following formula 5 is preliminarily measured:

$$\alpha = (S/S')^{1/2} = V0/V0' \quad (5)$$

By multiplying $\alpha$ by $V_0'$, fluctuation between the samples is removed. Specifically, once the reference voltage $V_0$ is determined at a reference temperature and a reference humidity, the value of a is calculated by measuring $V_0'$ for every sample at the reference temperature and the reference humidity.

On the other hand, S, T, and R are the constants and, from the formula 3 and the formula 5, the following formula 6 is therefore given:

$$\Delta V_0 = \{[R(T-T_0)/(\alpha \cdot S)]^{1/2} \cdot \Delta\alpha - [R \cdot \alpha S/(T-T_0)^{1/2} \cdot \Delta T_0]\}/2 \quad (6)$$

A function $f_1$ for $V_0$ and $T_0$ is represented by the following formula 7:

$$f_1 V - k_1 \cdot T_0 \quad (7)$$

$f_1$ can be represented by the following formula 8:

$$\Delta f_1 = \{[R(T-T_0)/(\alpha \cdot S)]^{1/2} \cdot \Delta\alpha - \quad (8)$$
$$[R \cdot \alpha \cdot S/(T-T_0) \, 1/2 \cdot \Delta T_0]\}/2 -$$
$$k_1 \cdot \Delta T_0$$

In the formula 8, in order to make $\Delta f_1$ be constant irrespective of variation of $\Delta T_0$, the value of $k_1$ is selected as the following formula 9:

$$k_1 = -[R \cdot \alpha \cdot S/(T-T_0)^{1/2} \cdot \Delta T_0]/2 \quad (9)$$

In this case, $\Delta f_1$ is represented by the following formula 10:

$$\Delta f_1 = [R(T-T_0)/(\alpha \cdot S)]^{1/2} \cdot \Delta\alpha]/2 \quad (10)$$

When the change in $T_0$ and $\alpha$ is small, $\Delta f_1$ depends on $\Delta\alpha$ (function of humidity) alone.

Description will now be made as regards a second correction method.

In the manner similar to the first correction method, $f_2$ is defined as the following formula 11:

$$f_2 = V^2 - k_2 \cdot T_0 \quad (11)$$

When $k_2 = R \cdot \alpha \cdot S$, $\Delta f_2$ is represented by the following formula 12:

$$\Delta f_2 = R \cdot S(T-T_0) \cdot \Delta\alpha \quad (12)$$

When the change in $T_0$ and $\alpha$ is small, $\Delta f_2$ depends on $\Delta\alpha$ (function of humidity) alone.

The correction device 4 corrects $V_0$ into $V_1$ by the above-mentioned first correction method or the above-mentioned second correction method.

Description will hereafter be made further in detail as regards the humidity sensor according to the one embodiment of this invention.

Figure 5:
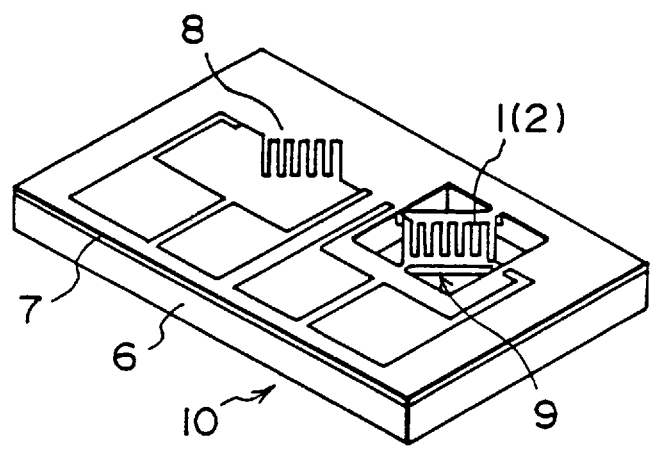
FIG. 5 is a perspective view showing a first example of a humidity sensor chip of FIG. 4.
Figure 6:
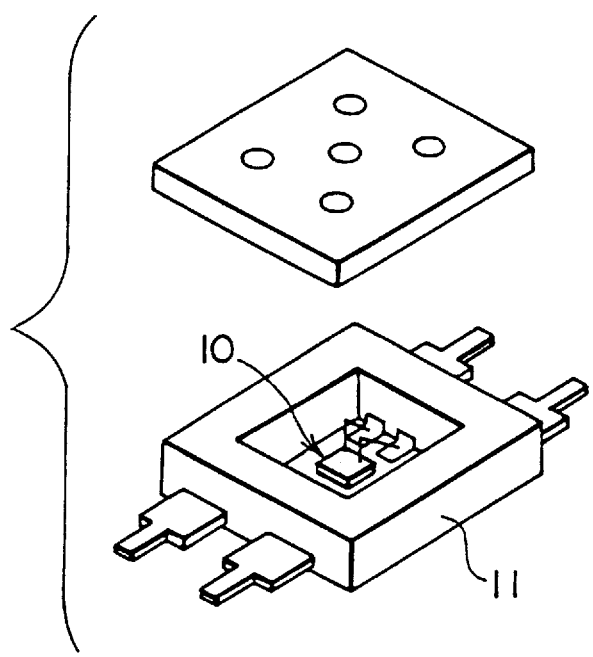
FIG. 6 is a perspective view showing the humidity sensor chip of FIG. 4 and a case.
Figure 7:
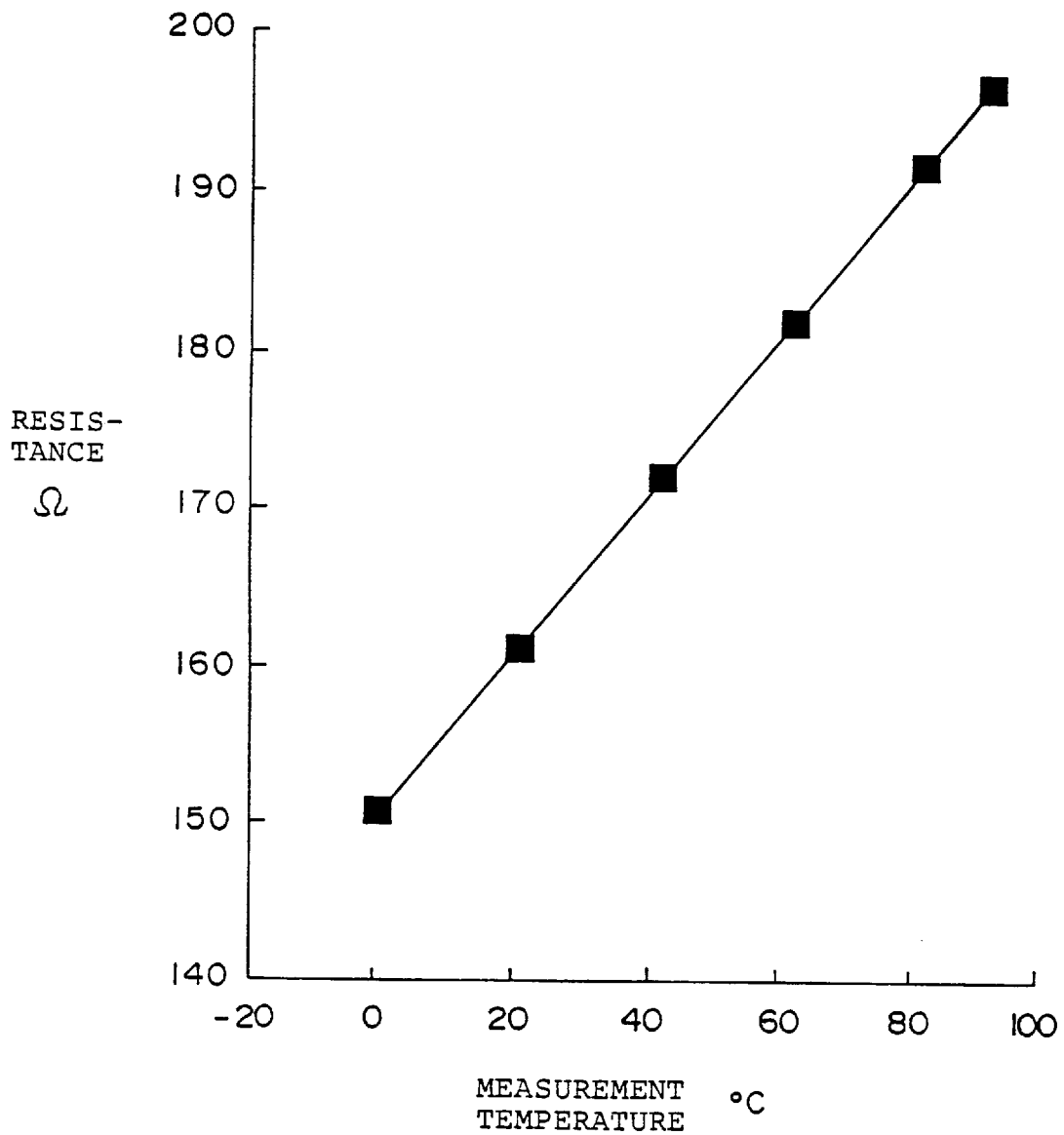
FIG. 7 through FIG. 12 are views for describing an operation of the humidity sensor illustrated in FIG. 4.

The temperature sensing resistor 1 is manufactured as follows. It is noted here that the one embodiment of this invention is directed to the case where the temperature sensing resistor 1 and the heat generator 2 are implemented by a single common element. Referring to FIG. 5, an $SiO_2$ film 7 is formed on a silicon substrate 6 to a thickness of 3 μm, for example, by a sputtering method. Next, a thin film platinum pattern is formed on the $SiO_2$ film 7 by the sputtering method, thereafter the temperature sensing resistor 1 and a temperature detecting resistor 8 are formed by the use of a photolithography technique. The temperature detecting resistor 8 forms the temperature detector 5. A portion of the $SiO_2$ film 7 that surrounds the temperature sensing resistor 1 is etched and removed by the use of the photolithography technique so that the temperature sensing resistor 1 is located on a bridge structure of the $SiO_2$ film 7. The temperature sensing resistor 1 and the member supporting the same form a humidity sensitive portion 9. Subsequently, a humidity sensor chip 10 is formed by cutting by the use of a dicing saw and the like. As shown in FIG. 6, the humidity sensor chip 10 thus obtained is fitted into a case 11. Thereafter, connecting terminals are connected by wire bonding or the like to complete the humidity sensor. The temperature sensing resistor 1 can be formed into an extremely small size so that the time constant can be reduced to several milliseconds. The temperature of the temperature sensing resistor 1 can be maintained at a constant level by applying a predetermined d.c. voltage from the power supply device 3 shown in FIG. 4 to the Wheatstone bridge circuit to flow a preselected current through the temperature sensing resistor 1, thereby generating the Joule heat. Referring to FIG. 7, the resistance-temperature characteristic of the temperature sensing resistor 1 has a one-to-one correspondence. Therefore, to keep the resistance value constant is to keep the temperature constant.

Figure 8:
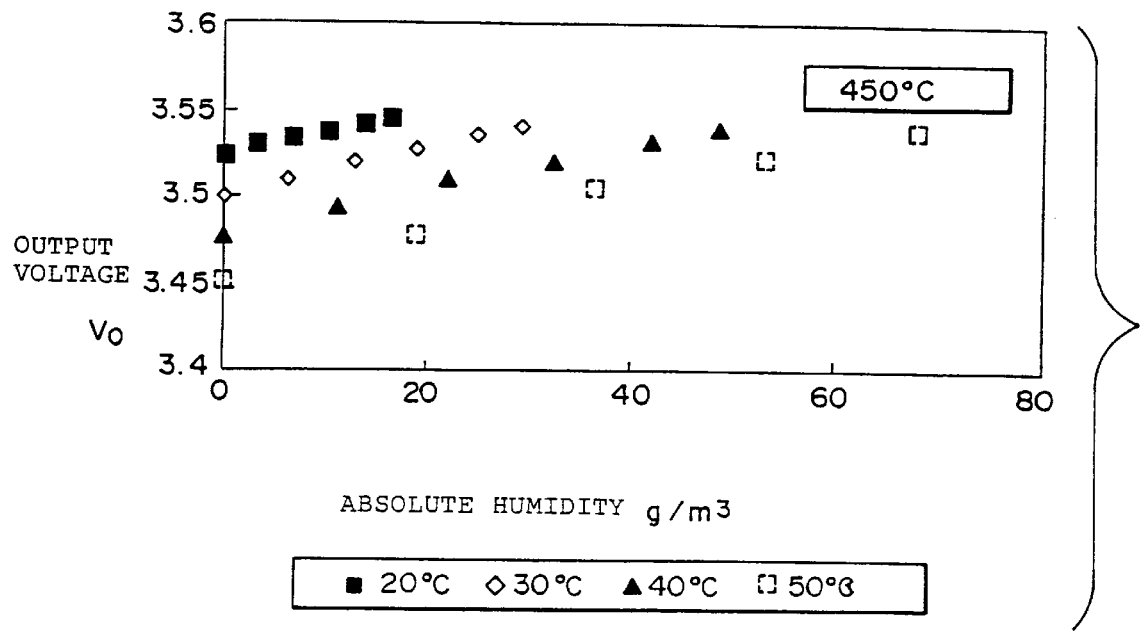
Figure 9:
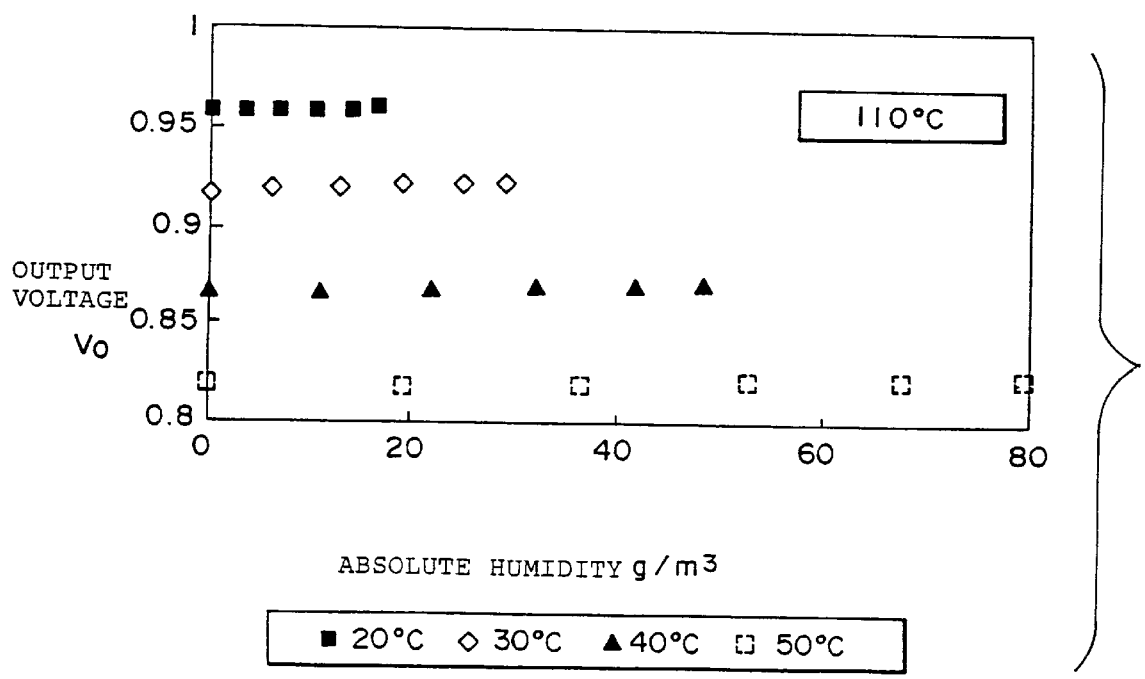

FIG. 8 and FIG. 9 show humidity characteristics of the output voltage $V_0$ of the Wheatstone bridge circuit when the temperature T of the temperature sensing resistor 1 is kept constant. FIG. 8 shows the output voltage $V_0$-humidity characteristic in the case where the temperature sensing resistor 1 is kept at a temperature of 450° C. and the temperature of the atmosphere is kept at constant values of 20° C., 30° C., 40° C., and 50° C. FIG. 9 shows the output voltage $V_0$-humidity characteristic in the case where the temperature sensing resistor 1 is kept at a temperature of 110° C. and the temperature of the atmosphere is kept at constant values of 20° C., 30° C., 40° C., and 50° C.

Figure 10:
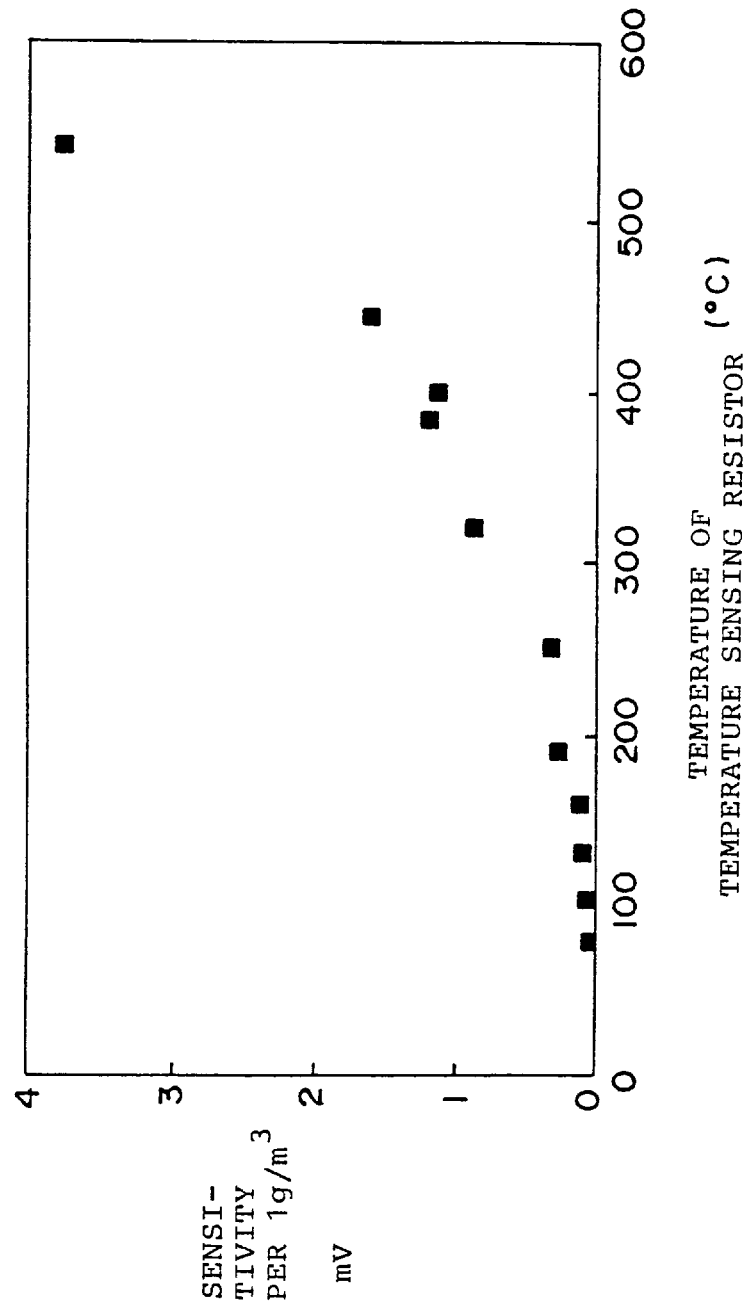

The experimental result on the characteristic of the sensitivity-temperature of the temperature sensing resistor is shown in FIG. 10. Herein, sensitivity=(the change in output voltage $V_0$)/(humidity) is defined. It is therefore necessary that the temperature T of the temperature sensing resistor 1 is held at 150° C. or more. The humidity characteristic of the output voltage $V_0$ depends on the temperature of the temperature sensing resistor 1. The higher the temperature of the temperature sensing resistor 1 is, the greater the sensitivity becomes.

When the temperature of the temperature sensing resistor 1 is between 100° C. and 150° C., the change in output voltage following the humidity change is substantially equal to 0. In other words, when the temperature of the temperature sensing resistor 1 is between 100° C. and 150° C., the output voltage does not depend on the humidity but on the temperature of the atmosphere and the humidity sensitive portion 9 of the sensor. This is also proved from the theoretical formula representing the vapor concentration dependency of the heat conductivity within the above-mentioned temperature range in the system containing water vapor mixed with pure air.

When the humidity is constant, the output voltage $V_0$ depending on the temperature $T_0$ of the atmosphere linearly changes with respect to the temperature $T_0$ of the atmosphere. The change rate of the output voltage depends on the temperature T of the temperature sensing resistor 1. The change rate ($\Delta V/\Delta T$) of the output voltage is represented by the following formula 13:

$$\Delta V/\Delta T = [R \cdot \beta \cdot \lambda/(T-T_0)]^{1/2} \quad (13)$$

Figure 11:
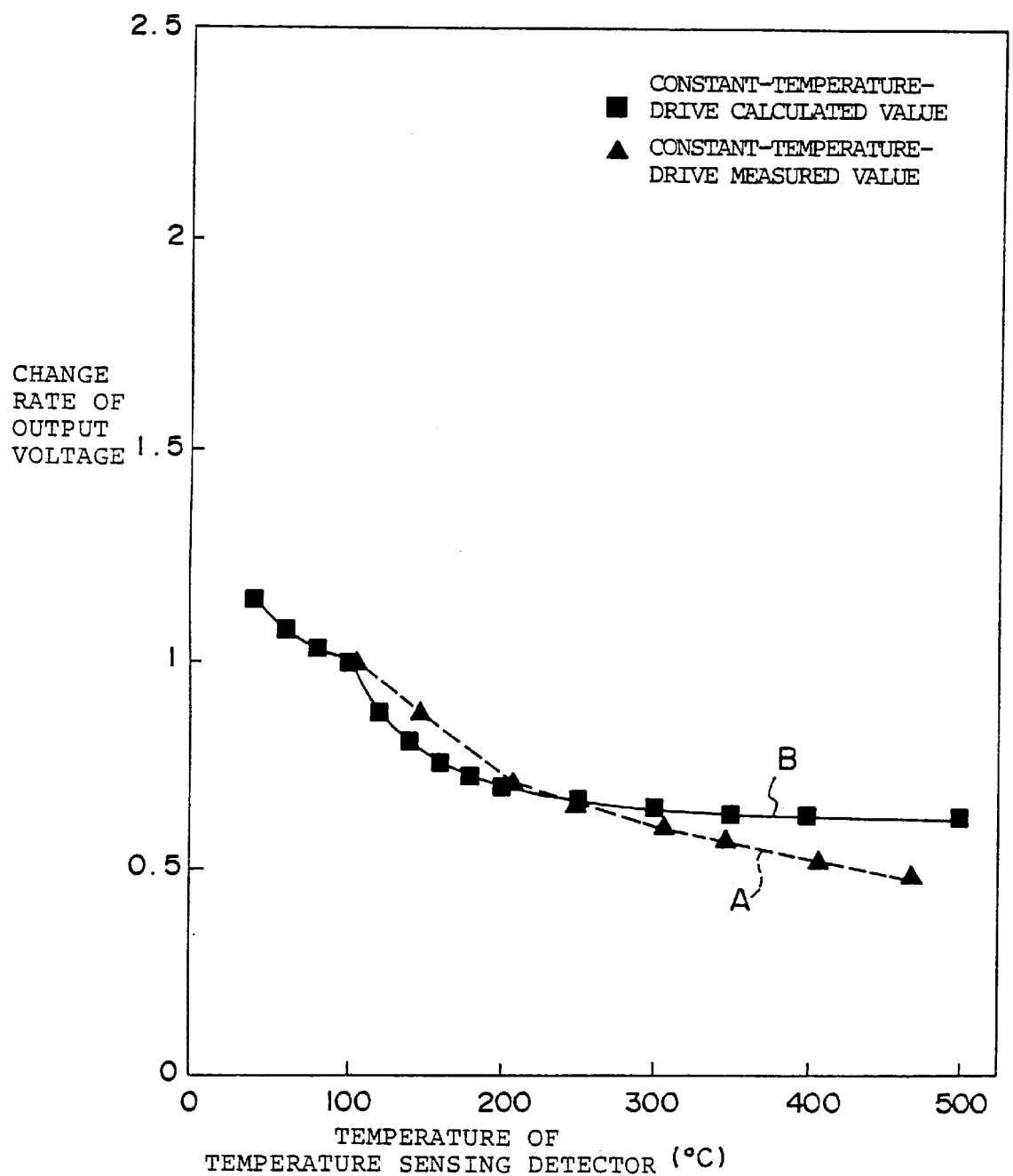

Because the value of β is unknown, the change rate is assumed to be equal to 1 when the temperature of the temperature sensing resistor 1 is 100° C. The measured values and the calculated values are shown in FIG. 11. In FIG. 11, the measured values (the constant-temperature-drive measured values) at the constant temperature of the temperature sensing resistor 1 are depicted by a curve A. On the other hand, the calculated values (the constant-temperature-drive calculated values) at the constant temperature of the temperature sensing resistor 1 is depicted by a curve B. From FIG. 11, it is understood that the constant-temperature-drive measured values and the constant-temperature-drive calculated values are substantially coincident in trend with each other.

The change rate of the output voltage is substantially constant when the temperature of the temperature sensing resistor 1 is 300° C. or more. It is therefore desired to maintain the temperature of the temperature sensing resistor 1 at a level of 300° C. or more. Also in view of burning of organic substances, it is desired to maintain the temperature of the temperature sensing resistor 1 at a level of 300° C. or more.

From the above-mentioned reasons, it is possible by constant-temperature driving to predict the change in output voltage $V_O$ depending on the temperature change of the measurement atmosphere. It is therefore possible to correct the output voltage $V_O$ with reference to the information of the temperature $T_O$ of the atmosphere.

Figure 12:
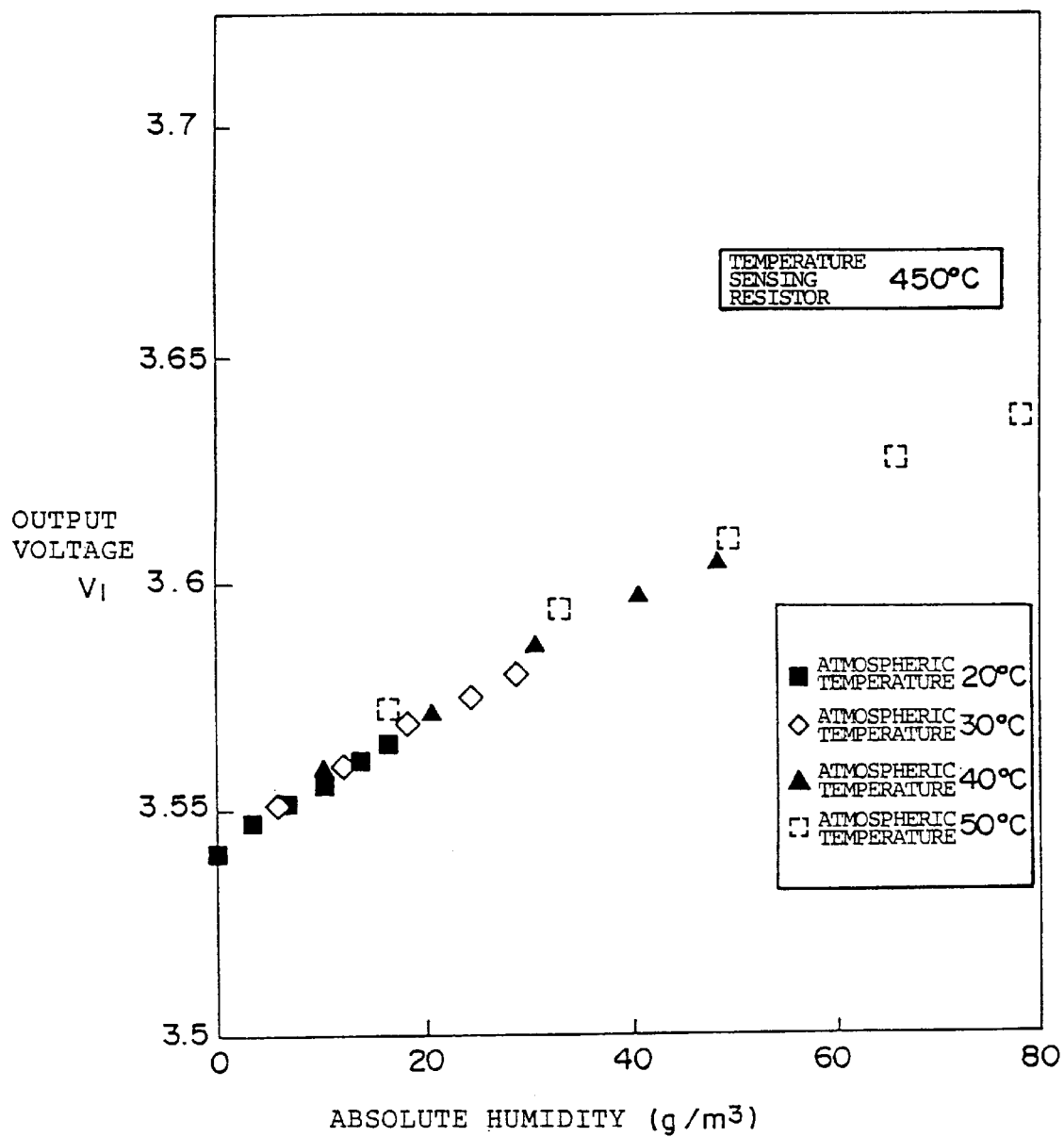

The above-mentioned correction by the correction device 4 may be carried out in an analogue fashion by a circuit or in a numerical calculation fashion by a microcomputer. FIG. 12 shows the output voltage-humidity characteristic after correction by the correction device 4. From FIG. 12, it is understood that the output voltage $V_1$ after correction by the correction device 4 is proportional to the humidity.

Now, description will be made as regards another example of the humidity sensor chip 10 with reference to FIG. 13 through FIG. 18.

Figure 2:
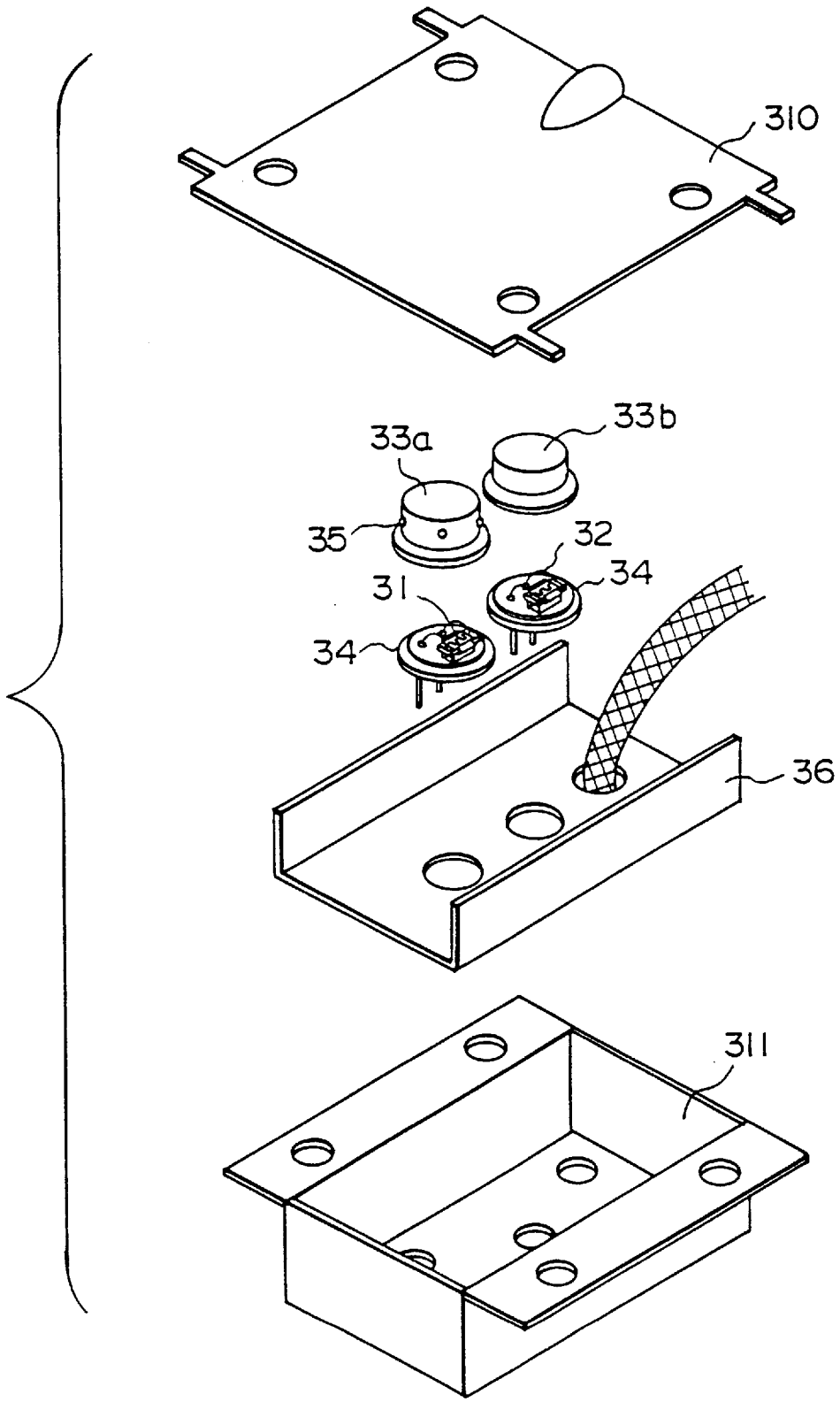
FIG. 2 is an exploded perspective view showing the conventional humidity sensor.
Figure 3:
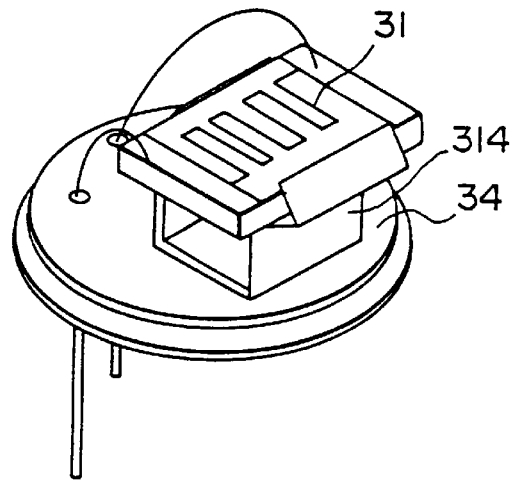
FIG. 3 is a perspective view showing a main portion of the conventional humidity sensor.
Figure 13:
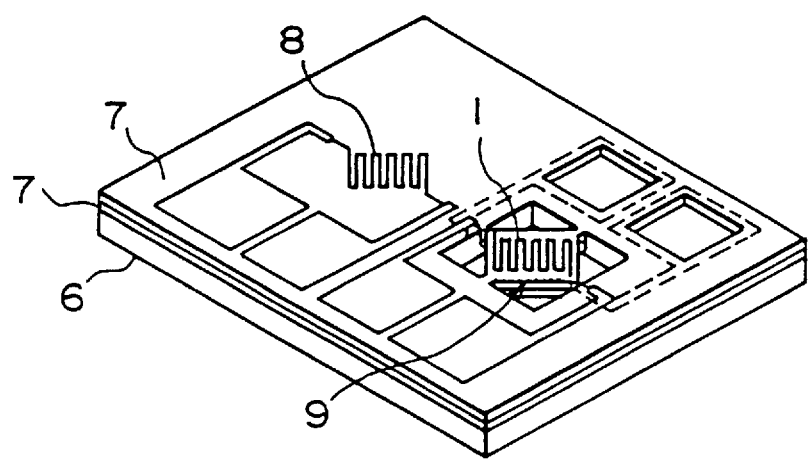
FIG. 13 is a perspective view showing a second example of the humidity sensor chip according to this invention.
Figure 14:
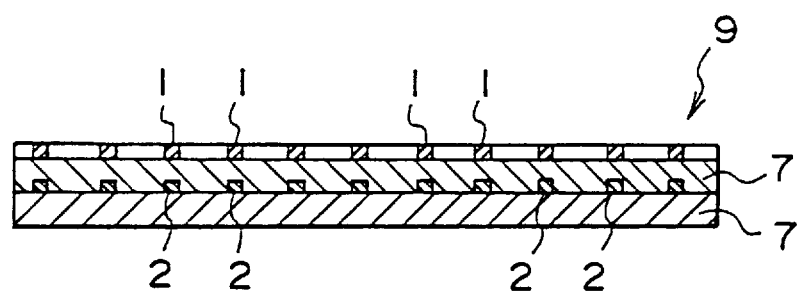
FIG. 14 is a sectional view showing the humidity sensor chip illustrated in FIG. 13.

The humidity sensor chip 10 shown in FIG. 13 and FIG. 14 comprises the thin film heat generator 2 formed on the $SiO_2$ film 7 and the thin film temperature sensing resistor 1 formed on the $SiO_2$ film 7 and the heat generator 2. The structure of the remaining portion is similar to that of the example shown in FIG. 2. Specifically, the humidity sensor chip 10 illustrated in FIG. 13 and FIG. 14 comprises the thin film heat generator 2 and the thin film temperature sensing resistor 1 as separate components integrally coupled.

Figure 15:
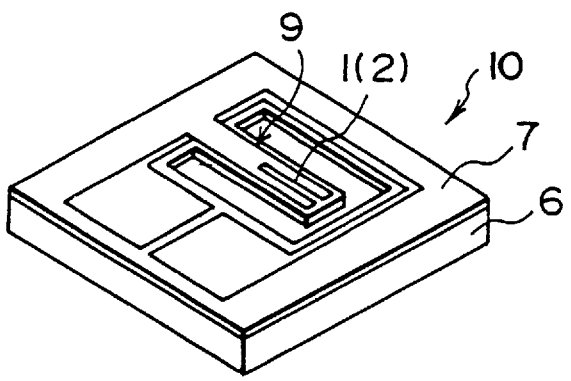
FIG. 15 is a perspective view showing a third example of the humidity sensor chip according to this invention.
Figure 16:
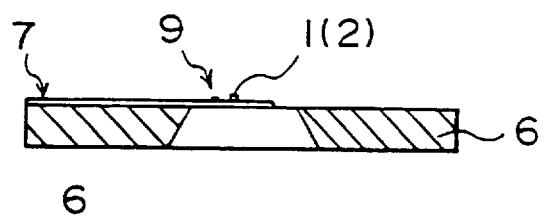
FIG. 16 is a sectional view showing the humidity sensor chip illustrated in FIG. 15.
Figure 17:
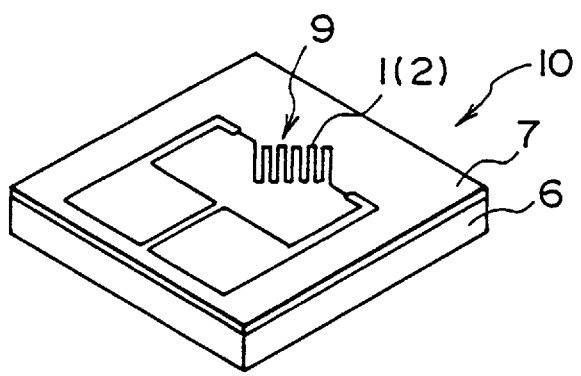
FIG. 17 is a perspective view showing a fourth example of the humidity sensor chip according to this invention.
Figure 18:
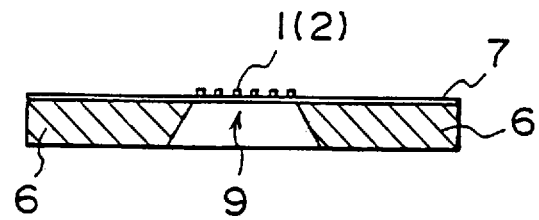
FIG. 18 is a sectional view showing the humidity sensor chip illustrated in FIG. 17.

A humidity sensor chip 10 shown in FIG. 15 and FIG. 16 comprises the humidity sensitive portion 9 formed in a cantilever structure. A humidity sensor chip 10 shown in FIG. 17 and FIG. 18 comprises the humidity sensitive portion 9 formed in a diaphragm structure.

The humidity sensor chip 10 of the humidity sensor according to one embodiment of this invention has an extremely small heat capacity and a time constant on the order of several milliseconds. It is therefore possible to save electric power by pulse driving on the order of 50 ms per one second.

In the one embodiment of this invention, the temperature sensing resistor 1 and the temperature detecting resistor 8 are formed on the same silicon substrate as described above. With this structure, it is possible to achieve reduction in size and cost.

It is noted here that this invention is not restricted to the Wheatstone bridge circuit but is applicable to any electronic circuit which produces the output voltage relating to the voltage drop of the temperature sensing resistor 1.

According to the one embodiment of this invention, the humidity measurement can be made by the use of a single temperature sensing resistor. This results in reduction of the change in characteristic depending on the change in temperature of the measurement atmosphere and in reduction of the cost.

Next, description will be made in detail as regards a humidity sensor according to another embodiment of this invention with reference to the drawing.

Figure 19:
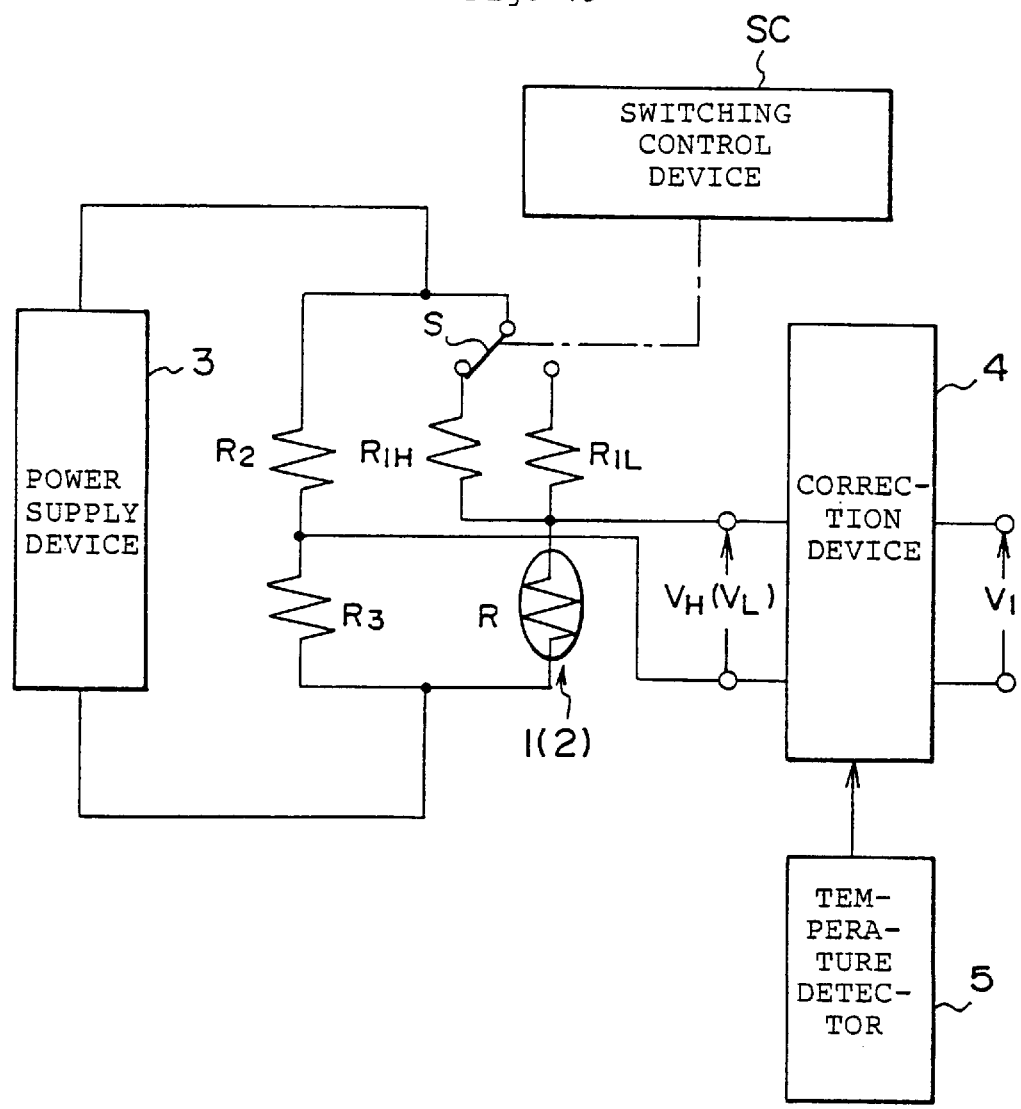
FIG. 19 is a circuit diagram showing a humidity sensor according to another embodiment of this invention.

FIG. 19 is a circuit diagram showing the humidity sensor according to another embodiment of this invention. As illustrated in FIG. 19, the humidity sensor according to another embodiment of this invention comprises the temperature sensing resistor 1 which also serves as the heat generator 2 and which has the resistance value R. The sensor also comprises three fixed resistors $R_{1L}$ or $R_{1H}$, $R_2$, and $R_3$. Herein, among the fixed resistors, $R_2=R_3$ is selected to be satisfied. The temperature sensing resistor 1 having the resistance value R and the three fixed resistors $R_{1L}$ or $R_{1H}$, $R_2$, and $R_3$ form the Wheatstone bridge circuit. The humidity is measured by utilizing the fact that the heat radiation of the temperature sensing resistor 1 changes depending on the humidity. The input terminal of the Wheatstone bridge circuit is connected to the power supply device 3. On the other hand, the output terminal of the Wheatstone bridge circuit is connected to the correction device 4. The correction device 4 is connected to the temperature detector 5 for detecting the temperature in the measurement atmosphere. The temperature detector 5 supplies the correction device 4 with the information of the temperature in the measurement atmosphere.

The power supply device 3 and the fixed resistors $R_2$ and $R_3$ are connected in series. Between the power supply device 3 and the temperature sensing resistor 1, the fixed resistors $R_{1L}$ and $R_{1H}$ are connected in parallel through a switch S. The operation of the switch S is controlled by a switching control device SC. The switching control device SC controls the operation of the switch S so as to connect the fixed resistor $R_{1L}$ or $R_{1H}$ with the power supply device 3 for every predetermined period.

The power supply device 3 applies the voltage to the temperature sensing resistor 1 through the switch S to flow the current, thereby generating Joule heat to keep the temperature sensing resistor 1 at the predetermined temperature as follows. Specifically, when the switch S connects the fixed resistor $R_{1H}$ with the power supply device 3, the temperature of the temperature sensing resistor 1 is kept at a first temperature of 300° C. or more for a short prescribed period, for example, several tens of milliseconds. When the switch S connects the fixed resistor $R_{1L}$ with the power supply device 3, the temperature is kept at a second temperature between 100° C. and 150° for a short prescribed period, for example, several tens of milliseconds. With reference to the output characteristic of the Wheatstone bridge circuit when the temperature of the temperature sensing resistor 1 is kept at the second temperature, the correction device 4 corrects an output voltage value $V_H$ of the Wheatstone bridge circuit when the temperature of the temperature sensing resistor 1 is kept at the first temperature, and produces the output voltage value $V_1$.

It is experimentally confirmed that, by flowing the current through the temperature sensing resistor 1 for several tens of milliseconds, the temperature of the temperature sensing resistor 1 can be kept at the first temperature of 300° C. or more and at the second temperature between 100° C. and 150°.

Description will be now made as regards a measurement principle of the humidity sensor according to another embodiment of this invention.

It is assumed that the temperatures of the temperature sensing resistor 1 and the humidity sensitive portion are approximately equal to each other. In this event, the temperature rise $\Delta T$ of the temperature sensing resistor 1 in a stationary state is represented by the above-mentioned formula 1. Let the temperature of the temperature sensing resistor 1 and the ambient temperature be represented by T and $T_0$ respectively. In this event, $\Delta T$ is represented by the above-mentioned formula 2. From the above-mentioned formulas 1 and 2, the formula 3 is obtained. Herein, $\alpha \cdot S$ is represented by the formula 4. The foregoing is same as the above-described humidity sensor of the one embodiment.

Between 100° C. and 150° C., the heat conductivity $\lambda$ hardly depends on the amount of water vapor within a humidity range between 0 and 300 g/m³. This is also proved from the theoretical formula representing the vapor concentration dependency of the heat conductivity $\lambda$ within the above-mentioned humidity range in the system containing water vapor mixed with pure air. Thus, the value of $V_0$ at a temperature between 100° C. and 150° C. does not depend on the humidity.

It is provided that the output voltage and the temperature when the temperature is not lower than 150° C. are represented by $V_H$ and $T_H$, respectively, and that the output voltage and the temperature when the temperature is between 100° C. and 150° C. are represented by $V_L$ and $T_L$, respectively. In this event, the information such as the ambient temperature $T_0$ and the shape effect S of the humidity sensitive portion, except the humidity H, is obtained by $V_L$. By using the condition as a reference, it is possible to measure the humidity H at a higher temperature $T_H$ (for example, 450° C.).

Next, description will be made as regards a first correction method of correcting $V_H$ into $V_1$.

The output voltages $V_H$ and $V_L$ are represented by the following formulas 14 and 15, respectively.

$$V_H = [\alpha_H \cdot S \cdot (T_H - T_0) \cdot R_H]^{1/2} \tag{14}$$

Herein, $\alpha_H$ represents $\alpha$ at the temperature $T_H$. $\alpha_H$ is a function of the humidity H alone because $T_H$ is maintained constant. $R_H$ represents R at the temperature $T_H$.

$$V_L = [\alpha_L \cdot S \cdot (T_L - T_0) \cdot R_L]^{1/2} \tag{15}$$

Herein, $\alpha_L$ represents $\alpha$ at the temperature $T_L$. $R_L$ represents R at the temperature $T_L$.

The value of S fluctuates depending on each sample. For a sample having, for example, the constant S' depending on the area and the shape of the humidity sensitive portion, the value of a in the following formula 16 is preliminarily measured with the output voltage of the Wheatstone bridge circuit being represented by $V_L'$.

$$a = (S/S')^{1/2} = V_L/V_L' \tag{16}$$

By multiplying the value a by $V_L'$, fluctuation between the samples is removed. Specifically, once the reference voltage $V_L$ is determined at a reference temperature, the value of a is calculated by measuring $V_L'$ for every sample at the reference temperature because the value of $V_L'$ dose not depend on humidity.

In the formulas 5 and 6, S, $T_H$, $R_H$, $\alpha_L$, $T_L$, and $R_L$ are the constants. Therefore, $\Delta V_H$ and $\Delta V_L$ are represented by the following formulas 17 and 18:

$$V_H = [\alpha_H \cdot S \cdot R_H(T_H - T_0)]^{1/2} \tag{17}$$
$$= [\alpha_H \cdot S \cdot R_H \cdot T_H(1 - T_0)/T_H]^{1/2}$$

$$V_L = [\alpha_L \cdot S \cdot (T_L - T_0) \cdot R_L]^{1/2} \tag{18}$$
$$= [\alpha_L \cdot S \cdot R_L \cdot T_L(1 - T_0/T_L)]^{1/2}$$

When $T_0/T_H$ and $T_0/T_L$ are far smaller than 1, the formulas 17 and 18 are rewritten into the following formulas 19 and 20:

$$V_H = [\alpha_H \cdot S \cdot R_H \cdot T_H]^{1/2}[1 - T_0/(2T_H)] \tag{19}$$

$$V_L = [\alpha_L \cdot S \cdot R_L \cdot T_L]^{1/2}[1 - T_0/(2T_L)] \tag{20}$$

Let the function $f_1$ for $V_H$ and $V_L$ be represented by the following formula 21:

$$f_1 = V_H - k_1 \cdot V_L \tag{21}$$

In this case, the change of $f_1$ depending on the change of $T_0$ is minimized, if $f_1$ satisfies the condition defined by the following formula 22:

$$\frac{\delta f_1}{\delta T_0} = 0 \tag{22}$$

The formulas 19, 20, and 22 lead to the following formula 23:

$$\frac{\delta f_1}{\delta T_0} = -\frac{1}{2T_L}(\alpha_H \cdot S \cdot R_H \cdot T_H)^{1/2} + \frac{k_1}{2T_H}(\alpha_L \cdot S \cdot R_L \cdot T_L)^{1/2} \tag{23}$$

If $k_1$ is selected so that this formula 22 holds, $k_1$ is represented by the following formula 24:

$$k_1 = [(\alpha_H \cdot R_H \cdot T_L)/(\alpha_L \cdot R_L \cdot T_H)]^{1/2} \tag{24}$$

In this case, $f_1$ is represented by the following formula 25:

$$f_1 = [(\alpha_H \cdot R_H \cdot T_L)/T_H]^{1/2}(T_H - T_L) \tag{25}$$

From this formula 25, it is understood that $f_1$ does not depend on $T_0$.

Next, description will be made as regards a second correction method.

In the manner similar to the first correction method, let the function $f_2$ for $V_H^2$ and $V_L^2$ be represented by the following formula 26:

$$f_2 = V^2 - k_2 \cdot T_0 \tag{26}$$

In this case, the change of $f_2$ depending on the change of $T_0$ is minimized, if $f_2$ satisfies the condition defined by the following formula 27:

$$\frac{\delta f_2}{\delta T_0} = 0 \tag{27}$$

The formulas 26 and 27 lead to the following formula 28:

$$\frac{\delta f_2}{\delta T_0} = -\alpha_H \cdot S \cdot R_H + k_2 \cdot \alpha_L \cdot S \cdot R_L = 0 \tag{28}$$

If $k_2$ is selected so that this formula 28 holds, $k_2$ is represented by the following formula 29:

$$k_2 = (\alpha_H \cdot R_H)/(\alpha_L \cdot R_L) \tag{29}$$

In this case, $f_2$ is represented by the following formula 30:

$$f_2 = \alpha_H \cdot S \cdot R_H(T_H - T_L) \tag{30}$$

From this formula 30, it is understood that $f_2$ does not depend on $T_0$.

With reference to the output characteristic of the Wheatstone bridge circuit when the temperature of the temperature sensing resistor 1 is kept at the second temperature between 100° C. and 150° C., the correction device 4 corrects the output voltage value $V_H$ of the Wheatstone bridge circuit when the temperature of the temperature sensing resistor 1 is kept at the first temperature of 300° C. or more by the first correction method or the second correction method.

Description will more specifically be made as regards the humidity sensor according to another embodiment of this invention. Since the temperature sensing resistor 1 is similar to the foregoing one embodiment of this invention, description of a manufacturing method thereof is omitted. Like the one according to the first embodiment, the temperature sensing resistor 1 can be formed into an extremely small size so that the time constant can be reduced to several milliseconds. Therefore, it is possible within one second to heat the temperature sensing resistor 1 to the two different temperatures followed by cooling.

The temperature of the temperature sensing resistor 1 can be maintained at a predetermined level by applying the predetermined d.c. voltage from the power supply device 3 shown in FIG. 19 to the Wheatstone bridge circuit to flow the preselected current through the temperature sensing resistor 1, thereby generating the Joule heat. The resistance-temperature characteristic of the temperature sensing resistor 1 has a one-to-one correspondence as shown in FIG. 4. Therefore, to keep the resistance value constant is to keep the temperature constant.

In the second embodiment, the temperature characteristic of the temperature sensing resistor is similar to the result shown in FIG. 7.

The humidity characteristic of the output voltage $V_H$ depends on the temperature of the temperature sensing resistor 1. The higher the temperature of the temperature sensing resistor 1 is, the greater the sensitivity becomes.

When the humidity is constant, the output voltage $V_H$ depending on the temperature $T_0$ of the atmosphere linearly changes with respect to the temperature $T_0$ of the atmosphere. The change rate of the output voltage depends on the temperature $T_H$ of the temperature sensing resistor 1. The change rate ($\Delta V/\Delta T$) of the output voltage is represented by the following formula 31:

$$\Delta V/\Delta T = [R \cdot \beta \cdot \lambda/(T_H - T_0)]^{1/2} \quad (31)$$

Because $\beta$ is unknown, the change rate is assumed to be equal to 1 when the temperature of the temperature sensing resistor 1 is 100° C.

The measured values and the calculated values in this case are similar to the result shown in FIG. 11.

By the reason similar to the first embodiment, it is possible by constant-temperature-driving to predict the change in output voltage $V_H$ depending on the temperature change of the measurement atmosphere. Therefore, the correction device 4 can correct the output voltage $V_H$ by the first correction method or the second correction method, with reference to the information of the temperature $T_0$ of the atmosphere and the output characteristic of the Wheatstone bridge circuit when the temperature of the temperature sensing resistor 1 is kept at the second temperature between 100° C. and 150° C.

As described above, in the second embodiment of this invention also, the humidity measurement can be made by one temperature sensing resistor. This results in reduction of the change in characteristic depending on the change in temperature of the measurement atmosphere and in reduction of the cost.

INDUSTRIAL APPLICABILITY

As described above, the humidity sensor according to this invention enables the humidity measurement by the use of a single temperature sensing resistor. It is therefore possible to reduce the change in characteristic depending on the change in temperature of the measurement atmosphere and to reduce the cost. Accordingly, the humidity sensor is applicable for measurement of the amount of water vapor in the atmosphere at the air conditioner, the dehumidifier, the cooker, the cultivation house, and so on.

We claim:

1. A humidity sensor for measuring humidity by utilizing the fact that the heat dissipation of a temperature sensing resistor changes depending on the humidity, said humidity sensor comprising:

a heating control unit which includes a heat generator for self-radiation of Joule heat and being arranged to heat said temperature sensing resistor, said heat generator being controlled by said heating control unit to heat said temperature sensing resistor to control the temperature of said temperature sensing resistor to be at a constant temperature as a constant first temperature, wherein said constant first temperature is more than 150° C.;

an electrical circuit for producing an output voltage relating to voltage drop across said temperature sensing resistor at said first temperature; and correcting means for correcting the output voltage value of the output voltage of said electrical circuit with reference to a variation in output voltage value of the output of said electrical circuit depending on the ambient temperature of said temperature sensing resistor.

2. A humidity sensor as claimed in claim 1, wherein said electrical circuit comprises a Wheatstone bridge circuit including said temperature sensing resistor.

3. A humidity sensor as claimed in claim 1, wherein said temperature sensing resistor and said heat generator comprise thin films and are formed in an integral body.

4. A humidity sensor as claimed in claim 1, wherein said temperature sensing resistor and said heat generator are made of a single common element comprising a thin film.

5. A humidity sensor as claimed in claim 1, wherein said first temperature is 300° C. or more.

6. A humidity sensor as claimed in claim 1, wherein:

said heating control unit comprises switching means for switching the temperature of said temperature sensing resistor between said first temperature and a second temperature lower than said first temperature by applying two kinds of pulse voltages to said heat generator within a predetermined period of time, said electrical circuit produces the output voltage relating to the voltage drop across said temperature sensing resistor when the temperature of said temperature sensing resistor is selected at said second temperature, and said correcting means corrects, with reference to the output characteristic of said electronic circuit, the output voltage value of said electrical circuit when the temperature of said temperature sensing resistor is selected at said first temperature, so as to remove the influence of the temperature of a measurement atmosphere.

7. A humidity sensor as claimed in claim 6, wherein said temperature sensing resistor and said heat generator comprise thin films and are formed in an integral body.

8. A humidity sensor as claimed in claim 6, wherein said temperature sensing resistor and said heat generator are made of a single common element comprising a thin film.

9. A humidity sensor as claimed in claim 6, wherein said electrical circuit comprises two kinds of resistor portions switched by said switching means for changing an applied voltage by said two kinds of pulse voltages applied to said temperature sensing resistor.

10. A humidity sensor as claimed in claim 6, wherein said correcting means comprises:
- a temperature detector for supplying temperature information of a measurement atmosphere; and
- a correction device for correcting said output voltage value with reference to the temperature information of the measurement atmosphere.

11. A humidity sensor as claimed in claim 6, wherein said heating control means comprises a power supply device for producing said two kinds of pulse voltages to heat said temperature sensing resistor which is thereby selectively kept at said first temperature and said second temperature.

12. A humidity sensor as claimed in claim 6, wherein said second temperature is a constant temperature within a range between 100° and 150° C.

* * * * *